United States Patent
Li et al.

(10) Patent No.: US 10,750,957 B2
(45) Date of Patent: Aug. 25, 2020

(54) CLAMP MECHANISM TO ASSIST IN ATTACHING A FINGER CUFF

(71) Applicant: Edwards Lifesciences Corporation, Irvine, CA (US)

(72) Inventors: Peiyuan Li, Almere (NL); Max Desiré Leonard Stotijn, Hoogeveen (NL)

(73) Assignee: Edwards Lifesciences Corporation, Irvine, CA (US)

( * ) Notice: Subject to any disclaimer, the term of this patent is extended or adjusted under 35 U.S.C. 154(b) by 672 days.

(21) Appl. No.: 15/582,262

(22) Filed: Apr. 28, 2017

(65) Prior Publication Data

US 2018/0310840 A1    Nov. 1, 2018

(51) Int. Cl.
  *A61B 5/022*     (2006.01)
  *A61B 5/00*      (2006.01)
  *A61B 5/021*     (2006.01)
  *A61B 5/1455*    (2006.01)

(52) U.S. Cl.
  CPC ...... *A61B 5/02241* (2013.01); *A61B 5/02141* (2013.01); *A61B 5/02233* (2013.01); *A61B 5/6838* (2013.01); *A61B 5/14552* (2013.01)

(58) Field of Classification Search
  CPC ............ A61B 5/02241; A61B 5/02233; A61B 5/6838; A61B 5/6826; A61B 5/02141; A61B 5/14552
  See application file for complete search history.

(56) References Cited

U.S. PATENT DOCUMENTS

| | | | |
|---|---|---|---|
| 2008/0171915 A1* | 7/2008 | Kawajiri | A61B 5/02241 600/300 |
| 2011/0040196 A1 | 2/2011 | Shih et al. | |
| 2011/0054330 A1* | 3/2011 | Pfeiffer | A61B 5/02225 600/490 |
| 2012/0004559 A1 | 1/2012 | Lee et al. | |
| 2012/0004560 A1 | 1/2012 | Sano et al. | |
| 2016/0000342 A1 | 1/2016 | Ito et al. | |

FOREIGN PATENT DOCUMENTS

| | | |
|---|---|---|
| DE | 102011055747 A1 | 5/2013 |
| WO | 2014017975 A1 | 1/2014 |

* cited by examiner

*Primary Examiner* — Devin B Henson
(74) *Attorney, Agent, or Firm* — Eric King; Womble Bond Dickinson (57) ABSTRACT

Disclosed is a clamp mechanism to assist in attaching a finger cuff to a patient's finger by a medical assistant. The clamp mechanism may comprise a mounting structure including a top portion having a gap, opposed descending sides, an exterior, and a pair of opposed clamping members. The pair of opposed clamping members extend from opposite sides of the exterior of the mounting structure to form a clamping slot over the gap. The clamping slot is openable by the medical assistant to allow for the pulling of the first side and the second side of the finger cuff by the medical assistant through the gap and the opened clamping slot. Further, the clamping slot is closeable by the medical assistant so that the first side and the second side of the finger cuff are clamped together such that the finger cuff is firmly attachable to the patient's finger.

27 Claims, 6 Drawing Sheets

CLAMP MECHANISM TO ASSIST IN ATTACHING A FINGER CUFF

BACKGROUND

Field

Embodiments of the invention may relate to a clamp mechanism to assist in attaching a finger cuff having a first side and a second side to a patient's finger by a medical assistant.

Relevant Background

Volume clamping is a technique for non-invasively measuring blood pressure in which pressure is applied to a subject's finger in such a manner that arterial pressure may be balanced by a time varying pressure to maintain a constant arterial volume. In a properly fitted and calibrated system, the applied time varying pressure is equal to the arterial blood pressure in the finger. The applied time varying pressure may be measured to provide a reading of the patient's arterial blood pressure.

This may be accomplished by a finger cuff that is arranged around a finger of a patient. The finger cuff may include an infrared light source, an infrared sensor, and an inflatable bladder. The infrared light may be sent through the finger in which a finger artery is present. The infrared sensor picks up the infrared light and the amount of infrared light registered by the sensor may be inversely proportional to the artery diameter and indicative of the pressure in the artery.

In the finger cuff implementation, by inflating the bladder in the finger cuff, a pressure is exerted on the finger artery. If the pressure is high enough, it will compress the artery and the amount of light registered by the sensor will increase. The amount of pressure necessary in the inflatable bladder to compress the artery is dependent on the blood pressure. By controlling the pressure of the inflatable bladder such that the diameter of the finger artery is kept constant, the blood pressure may be monitored in very precise detail as the pressure in the inflatable bladder is directly linked to the blood pressure. In a typical present day finger cuff implementation, a volume clamp system is used with the finger cuff. The volume clamp system typically includes a pressure generating system and a regulating system that includes: a pump, a valve, and a pressure sensor in a closed loop feedback system that are used in the measurement of the arterial volume. To accurately measure blood pressure, the feedback loop provides sufficient pressure generating and releasing capabilities to match the pressure oscillations of the subject's blood pressure.

Unfortunately, finger cuffs are presently very difficult to attach to a patient's finger by a medical assistant. Typically, the attachment of a finger cuff by a medical assistant requires the use of two hands by the medical assistant to apply the finger cuff to a patient's finger, in which, one hand presses on one side of the finger cuff, while another hand pulls the other side of the finger cuff towards the same direction and then connects the two sides of the finger cuff together. It would be beneficial to both medical assistants and patients to have an easier way to attach the finger cuff to a patient's finger.

SUMMARY

Embodiments of the invention may relate to a clamp mechanism to assist in attaching a finger cuff having a first side and a second side to a patient's finger by a medical assistant. The clamp mechanism may comprise: a mounting structure including a top portion, opposed descending sides, and an exterior and an interior, wherein the top portion includes a gap; and a pair of opposed clamping members. The pair of opposed clamping members may extend from opposite sides of the exterior of the mounting structure to form a clamping slot over the gap. The clamping slot is openable by the medical assistant to allow for the pulling of the first side and the second side of the finger cuff by the medical assistant through the gap and the opened clamping slot. Further, the clamping slot is closeable by the medical assistant so that the first side and the second side of the finger cuff are clamped together such that the finger cuff is firmly attachable to the patient's finger.

DETAILED DESCRIPTION

Embodiments of the invention may relate to a finger cuff attachment system, apparatus, and method in which a clamp mechanism may be utilized by a medical assistant to assist in attaching a finger cuff to a patient's finger. By utilizing the techniques of this system, apparatus, and method, attaching a finger cuff to a patient's finger is made much easier than currently utilized techniques. Further, because the attachment time period to attach the finger cuff is shortened, the time period to obtain blood pressure measurements is significantly quicker than previous utilized techniques. Moreover, as will be described, by utilizing the embodiments of the invention, a one-size-fits-all finger cuff may be used instead of common place small, medium, and large sized finger cuffs.

Figure 1:
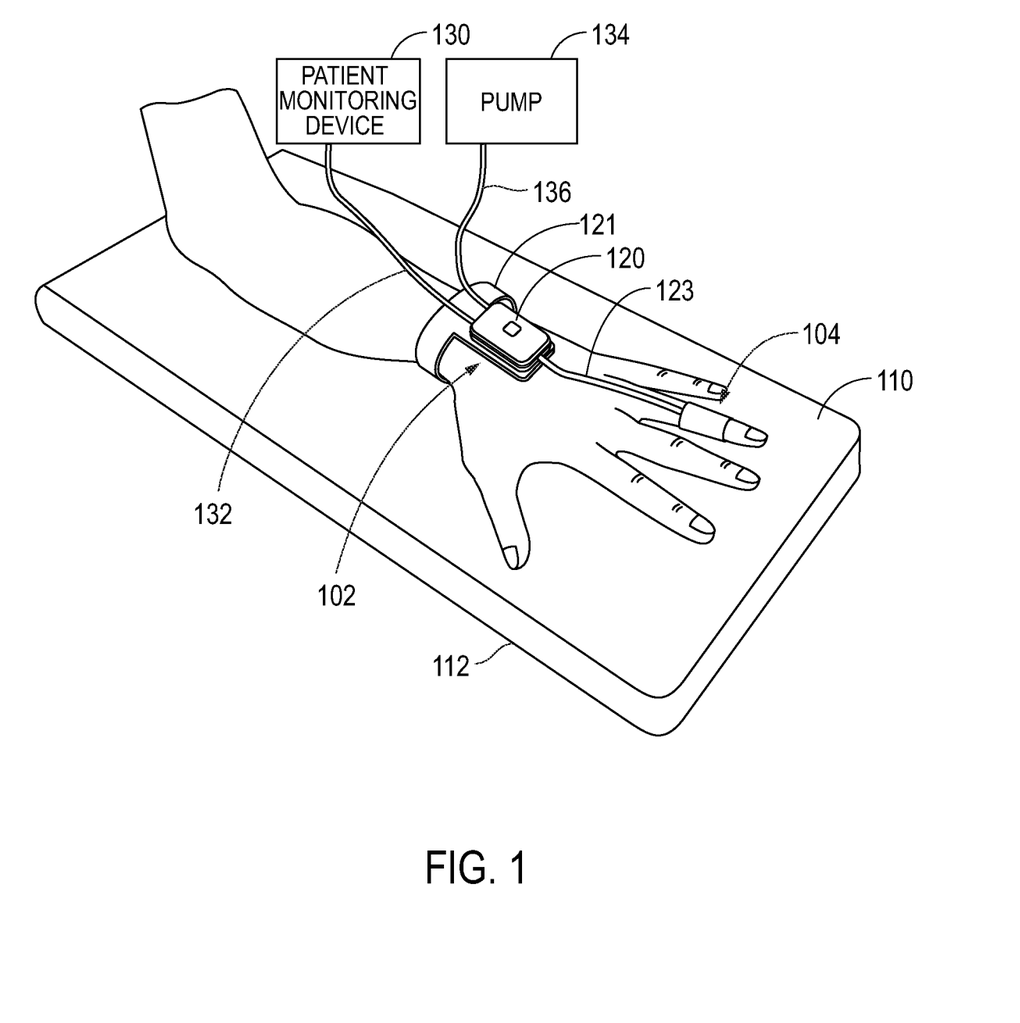
FIG. 1 is a diagram of an environment in which a finger cuff of a blood pressure measurement system may be implemented.

With reference to FIG. 1, an example of an environment in which a finger cuff 104 may be implemented will be described. As an example, a blood pressure measurement system 102 that includes a finger cuff 104 that may be attached to a patient's finger and a blood pressure measurement controller 120 that may be attached to the patient's body (e.g., a patient's wrist or hand) is shown. The blood pressure measurement system 102 may further be connected to a patient monitoring device 130, and, in some embodiments, a pump 134. Further, finger cuff 104 may include a bladder (not shown) and an LED-PD pair (not shown), which are conventional for finger cuffs.

In one embodiment, the blood pressure measurement system 102 may include a pressure measurement controller 120 that includes: a small internal pump, a small internal valve, a pressure sensor, and control circuity. In this embodiment, the control circuitry may be configured to: control the pneumatic pressure applied by the internal pump to the bladder of the finger cuff 104 to replicate the patient's blood pressure based upon measuring the pleth signal received from the LED-PD pair of the finger cuff 104. Further, the control circuitry may be configured to: control the opening of the internal valve to release pneumatic pressure from the bladder; or the internal valve may simply be an orifice that is not controlled. Additionally, the control circuitry may be configured to: measure the patient's blood pressure by monitoring the pressure of the bladder based upon the input from a pressure sensor, which should be the same as patient's blood pressure, and may display the patient's blood pressure on the patient monitoring device 130. This type of blood pressure measurement controller 120 is described in detail in Applicant's filed U.S. Provisional Patent Application Ser. No. 62/484,092, which is hereby incorporated by reference in its entirety.

In another embodiment, a conventional pressure generating and regulating system may be utilized, in which, a pump 134 is located remotely from the body of the patient. In this embodiment, the blood pressure measurement controller 120 receives pneumatic pressure from remote pump 134 through tube 136 and passes on the pneumatic pressure through tube 123 to the bladder of finger cuff 104. Blood pressure measurement device controller 120 may also control the pneumatic pressure (e.g., utilizing a controllable valve) applied to the finger cuff 104 as well as other functions. In this example, the pneumatic pressure applied by the pump 134 to the bladder of finger cuff 104 to replicate the patient's blood pressure based upon measuring the pleth signal received from the LED-PD pair of the finger cuff 104 and measuring the patient's blood pressure by monitoring the pressure of the bladder may be controlled by the blood pressure measurement controller 120 and/or a remote computing device and/or the pump 134 and/or the patient monitoring device 130. In some embodiments, a blood pressure measurement controller 120 is not used at all and there is simply a connection from the tube 123 to finger cuff connector 122 from a remote pump 134 including a remote pressure regulatory system, and all processing for the pressure generating and regulatory system, data processing, and display is performed by a remote computing device.

Continuing with this example, as shown in FIG. 1, a patient's hand may be placed on the face 110 of an arm rest 112 for measuring a patient's blood pressure with the blood pressure measurement system 102. The blood pressure measurement controller 120 of the blood pressure measurement system 102 may be coupled to a bladder of the finger cuff 104 in order to provide pneumatic pressure to the bladder for use in blood pressure measurement. Blood pressure measurement controller 120 may be coupled to the patient monitoring device 130 through a power/data cable 132. Also, in one embodiment, as previously described, in a remote implementation, blood pressure measurement controller 120 may be coupled to a remote pump 134 through tube 136 to receive pneumatic pressure for the bladder of the finger cuff 104. The patient monitoring device 130 may be any type of medical electronic device that may read, collect, process, display, etc., physiological readings/data of a patient including blood pressure, as well as any other suitable physiological patient readings. Accordingly, power/data cable 132 may transmit data to and from patient monitoring device 130 and also may provide power from the patient monitoring device 130 to the blood pressure measurement controller 120 and finger cuff 104.

As can be seen in FIG. 1, in one example, the finger cuff 104 may be attached to a patient's finger and the blood pressure measurement controller 120 may be attached on the patient's hand or wrist with an attachment bracelet 121 that wraps around the patient's wrist or hand. The attachment bracelet 121 may be metal, plastic, Velcro, etc. It should be appreciated that this is just one example of attaching a blood pressure measurement controller 120 and that any suitable way of attaching a blood pressure measurement controller to a patient's body or in close proximity to a patient's body may be utilized and that, in some embodiments, a blood pressure measurement controller 120 may not be used at all. It should further be appreciated that the finger cuff 104 may be connected to a blood pressure measurement controller described herein, or a pressure generating and regulating system of any other kind, such as a conventional pressure generating and regulating system that is located remotely from the body of the patient (e.g., a pump 134 located remotely from a patient). Any kind of pressure generating and regulating system that can be used, including but not limited to the blood pressure measurement controller, may be described simply as a pressure generating and regulating system. As a further example, in some embodiments, there may be no blood pressure measurement controller, at all, and a remote pump 134 that is controlled remotely may be directly connected via a tube 136 and 123 to finger cuff 104 to provide pneumatic pressure to the finger cuff 104.

Figure 2:
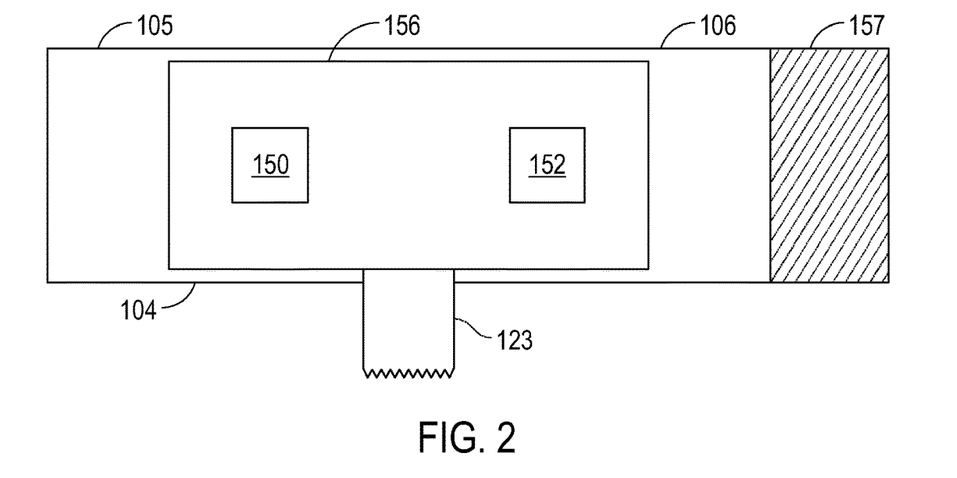
FIG. 2 is a diagram of an example finger cuff.

With additional reference to FIG. 2, an example finger cuff 104 is described. Finger cuff 104 may include a first side 105 and a second side 106. In one example, for attachment purposes to a patient's finger, the second side 106 on the interior may have a first Velcro-type hook-and-loop fastener portion 157 that connects with a second, corresponding Velcro-type hook-and-loop fastener portion on the exterior of the first side 105 of the finger cuff 104. It should be appreciated that this is just one example of an attachment mechanism and that any suitable type may be utilized. Further, finger cuff 104 may have a bladder 156 and an LED-PD pair 150 and 152. Tube 123 may be connected to bladder 156. It should be appreciated that this is just one example of a finger cuff 104 and that any suitable finger cuff may be utilized with embodiments of the invention.

Figure 3A:
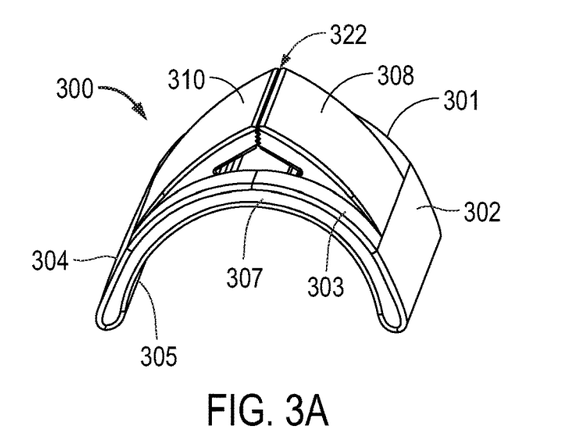
FIGS. 3A-3C are views of the clamp mechanism according to embodiments of the invention.
Figure 3B:
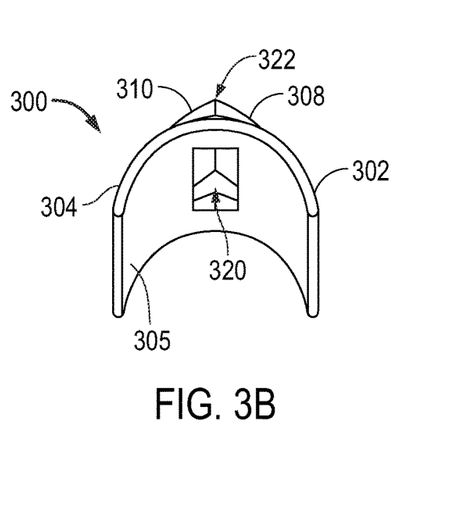
Figure 3C:
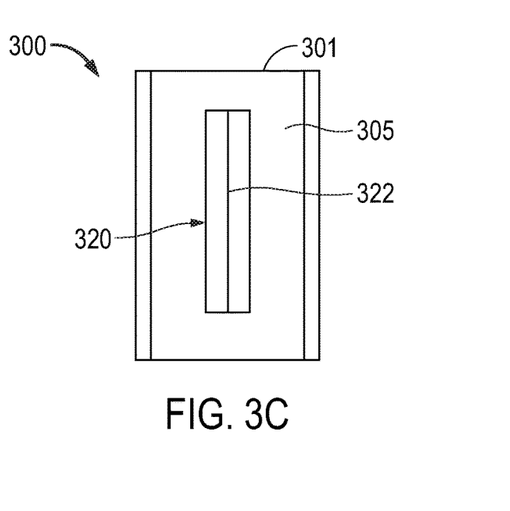

With additional reference to FIGS. 3A-3C, embodiments of the invention may relate to a clamp mechanism 300 to assist in attaching a finger cuff 104 having a first side and a second side 105 and 106 to a patient's finger by a medical assistant. The clamp mechanism 300 may comprise a mounting structure 301 that includes: opposed descending sides 302 and 304, and an exterior surface and an interior surface 303 and 305, in which, a top portion 307 of the mounting structure 301 includes an open gap 320. Further, the clamp mechanism 300 may include a pair of opposed clamping members 308 and 310. The pair of opposed clamping members 308 and 310 may extend from opposite sides of the exterior 303 of the mounting structure 301 from the opposed descending sides 302 and 304, respectively, such that they form a clamping slot 322 over the gap 320.

As will be described, the clamping slot 322 is openable by the medical assistant to allow for the pulling of the first side and the second side 105 and 106 of the finger cuff 104 by the medical assistant through the gap 320 and the opened clamping slot 322. Further, the clamping slot 322 is closeable by the medical assistant such that the first side and the second side 105 and 106 of the finger cuff 104 are clamped together so that the finger cuff 104 is firmly attached to the patient's finger.

As can be seen in FIGS. 3A-3C, a first embodiment of the clamp mechanism 300 to assist in attaching a finger cuff 104 having a first side 105 and second side 106 to a patient's finger by a medical assistant is shown. The attachment methodology of the finger cuff 104 by a medical assistant will be further described in more detail hereafter. In this embodiment, the clamp mechanism 300 may include a mounting structure 301 and a pair of opposed clamping members 308 and 310. The mounting structure 301 may include a top portion 307 and pair of opposed descending sides 302 and 304. Moreover, the mounting structure 301 may have an exterior surface 303 and an interior surface 305. Further, the top portion 307 of mounting structure 301 may include an open gap 320.

In one embodiment, the pair of opposed clamping members 308 and 310 may extend from opposite sides of the exterior surface 303 of the mounting structure 301 to form a clamping slot 322 over the open gap 320. As will be described, the clamping slot 322 is openable by a medical assistant to allow for the pulling of the first side and the second side 105 and 106 of the finger cuff 104 by a medical assistant through the open gap 320 and the opened clamping slot 322, when the finger cuff 104 is being attached to a patient's finger. Further, as will be described, clamping slot 322 is closable when the finger cuff is being attached to a patient's finger, such that the first side and the second side 105 and 106 of the finger cuff 104 are clamped together so that the finger cuff 104 is firmly attached to the patient's finger. In one embodiment, as can be particularly seen in FIG. 3A, both of the edges of the sidewalls of the opposed clamping members 308 and 310 to form the clamping slot 322 may have a saw-tooth like structure to increase friction between the mounting structure 301 and the first and second sides 105 and 106 of the finger cuff 104, and as a result, the finger cuff 104 can be more firmly clamped and more firmly attached to the patient's finger, as will be described in more detail hereafter. It should be appreciated that a saw-tooth like structure is just one example. As other examples, any type of interlocking structure, rough texture structure, or any type of structure or material (e.g., magnetic material) to increase the firmness between the mounting structure 301 and the finger cuff 104 in the clamping slot 322 may be utilized. Or a simple flat structure may be utilized with no enhanced structures or materials.

As can be seen in FIGS. 3A-3C, the mounting structure 301 including the opposed descending sides 302 and 304 may be approximately arch-shaped. Further, the opposed clamping members 308 and 310 may each extend from the exterior surface 303 of the opposed descending sides 302 and 304 of the arch-shaped mounting structure 301, respectively, to form an approximately triangle shape over the open gap 320 such that the clamping slot 322 is provided over the open gap 320.

Figure 4A:
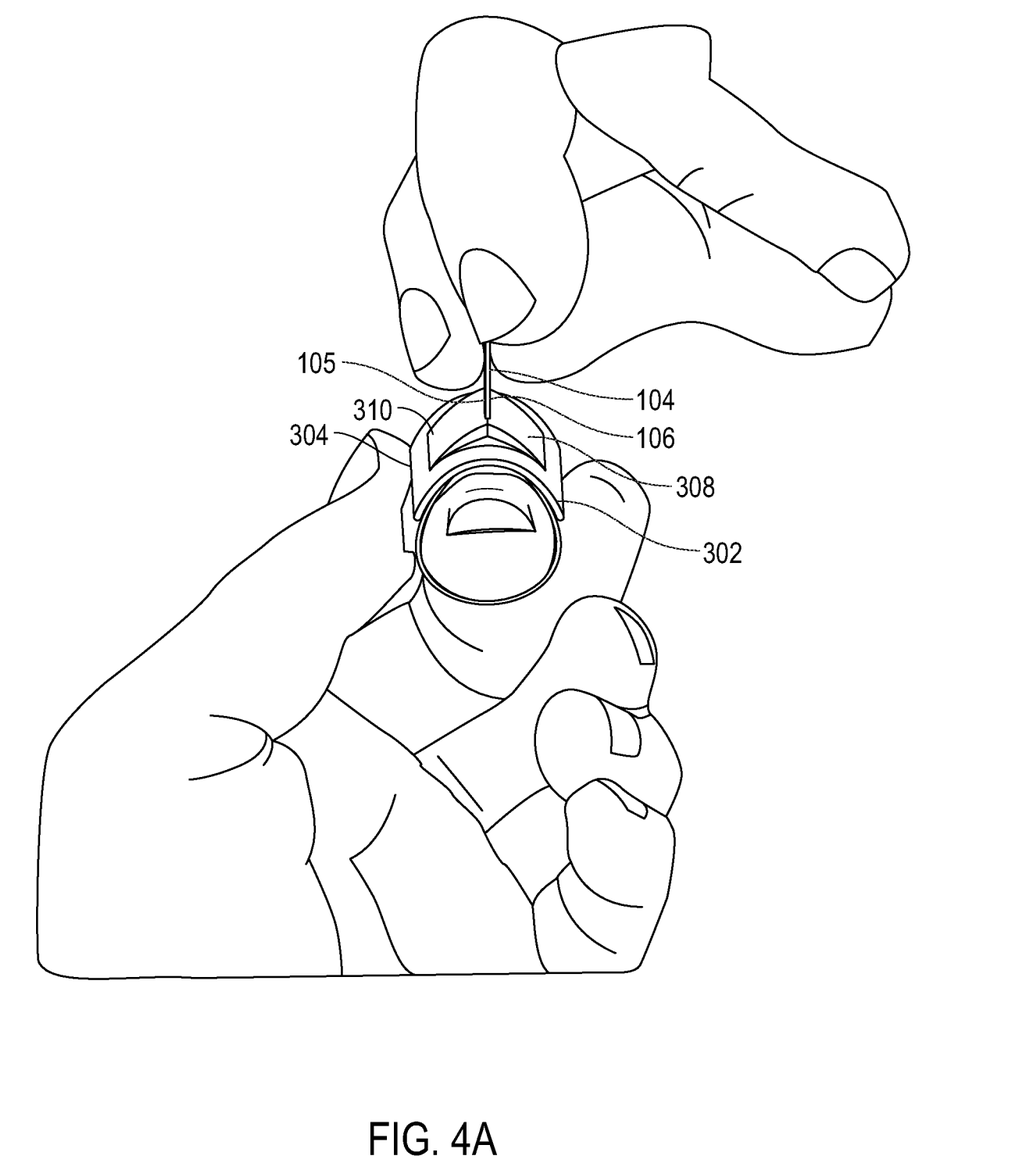
FIGS. 4A-4B are diagrams illustrating applying a finger cuff utilizing the clamp mechanism to assist in attaching the finger cuff to a patient's finger by a medical assistant.
Figure 4B:
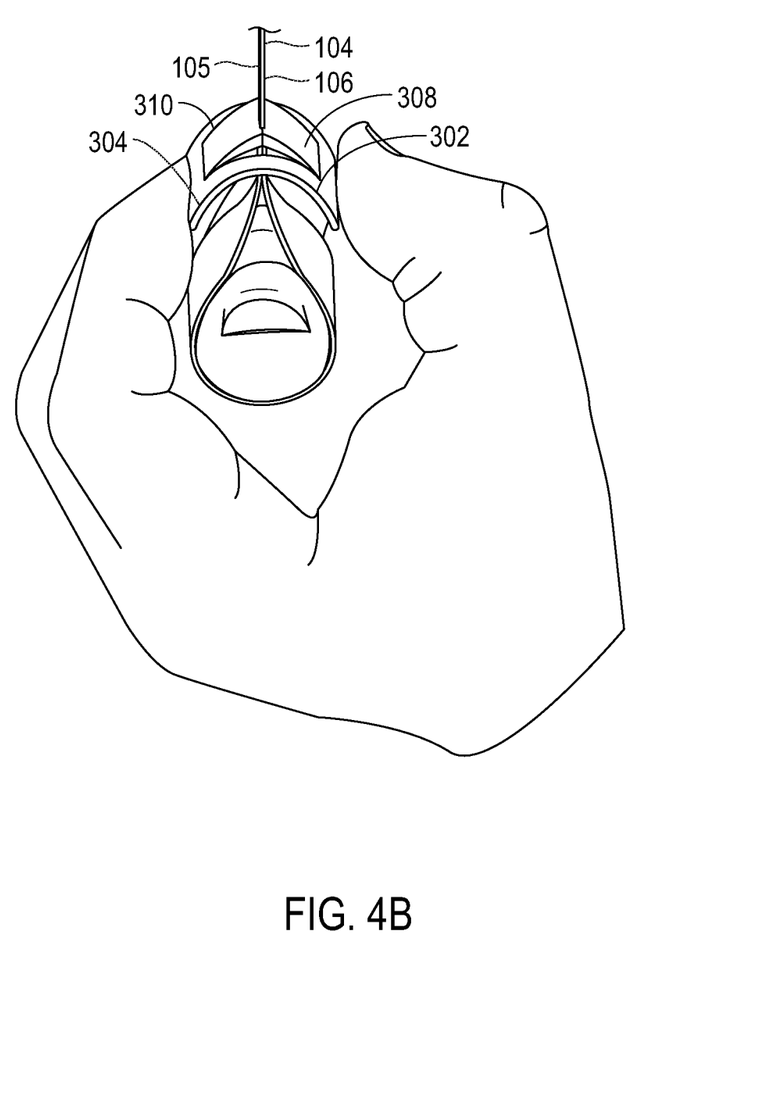

With additional reference to FIGS. 4A-4B, an illustration of applying a finger cuff 104 utilizing the clamp mechanism 105 to assist in attaching the finger cuff 104 having a first side and a second side 105 and 106 to a patient's finger by a medical assistant will be described. As can be seen in FIG. 4A, the opposed descending sides 302 and 304 of the mounting structure 301 may be suitably flexible to allow for the opening of the clamping slot 322 formed by the clamping members 308 and 310 when pressure is applied by the medial assistant to the opposed descending sides 302 and 304 to allow for the medical assistant to pull the first and second sides 105 and 106 of the finger cuff 104 through the opened clamping slot 322. Likewise, the opposed descending sides 302 and 304 of the mounting structure 301 are also suitably flexible to allow the clamping members 308 and 310 to close the clamping slot 322 to hold the first and second sides 105 and 106 of the finger cuff 104 firmly together when pressure is no longer applied by the medical assistant to the opposed descending sides 105 and 106 such that the finger cuff 104 is firmly attached to the patient's finger. In this way, the finger cuff 104 may be easily attachable to a patient's finger.

Also, it should be appreciated that releasing the finger cuff 104 from a patient's finger is also made easy. This may occur in the opposite way of applying the finger cuff. In particular, as can be seen in FIG. 4B, the opposed descending sides 302 and 304 of the mounting structure 301 are suitably flexible to allow for the opening of the clamping slot 322 formed by the clamping members 308 and 310 by the medical assistant applying pressure to the opposed descending sides 302 and 304 such that the clamp mechanism may be easily taken away from the first and second sides 105 and 106 of the finger cuff 104 and completely removed from the finger cuff 104 such that the finger cuff is no longer firmly attached to the patient's finger and can thereafter be removed.

Figure 5:
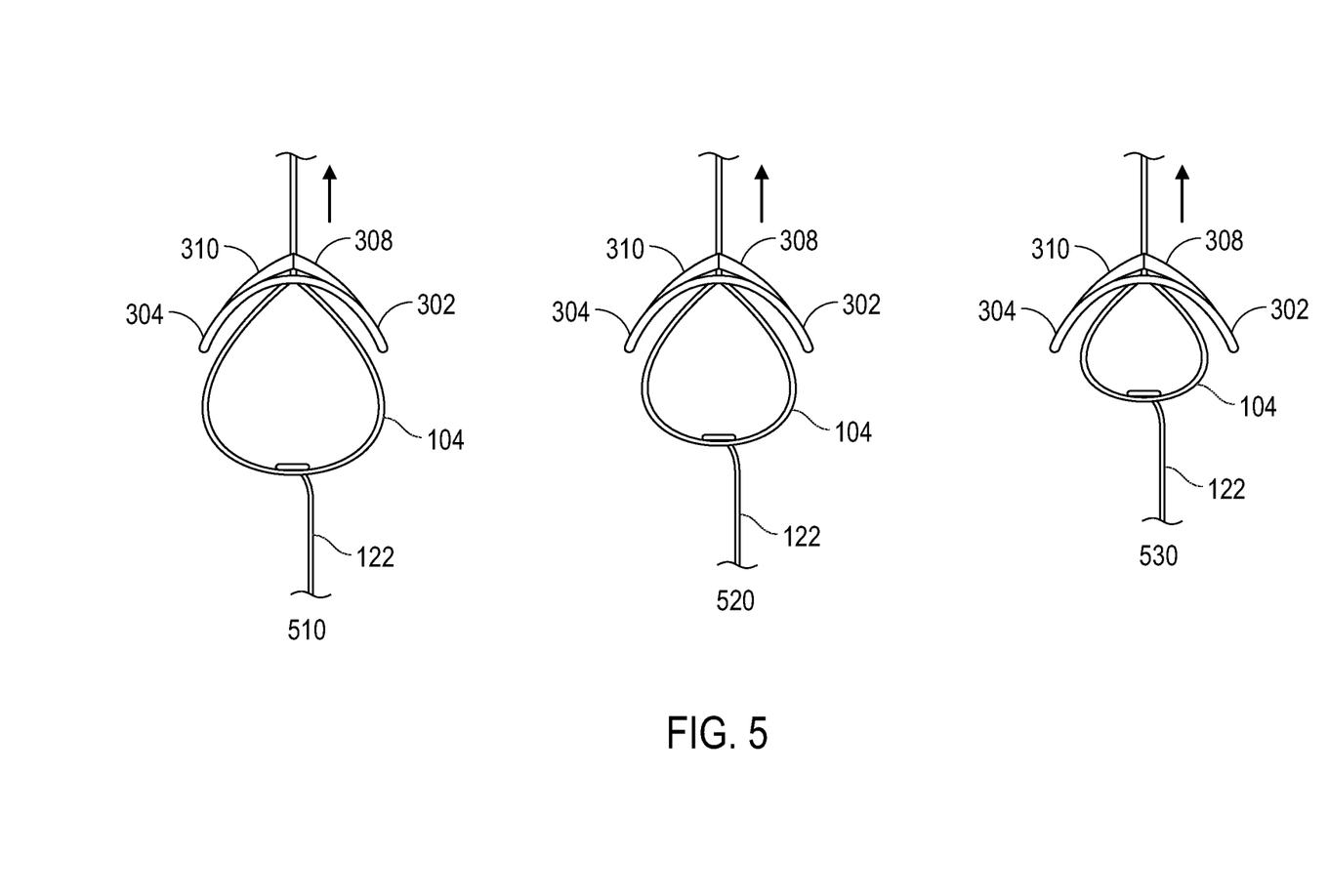
FIG. 5 is a diagram showing that a finger cuff may be differently sized for different finger sizes.

With additional reference to FIG. 5, FIG. 5 shows that by utilizing the finger clamp mechanism, a finger cuff 104 may be utilized that is adjustable as to size, such that a finger cuff 104 may be utilized for any finger size of the patient. In particular, a finger cuff 104 may be utilized that is sufficiently long enough to cover all potential finger size dimensions. Therefore, the clamp mechanism in combination with the finger cuff 104 provides a one-size-fits-all solution. As has been previously described, a medical assistant may apply pressure to the opposed descending sides 302 and 304 of the mounting structure to allow for the opening of the clamping slot 322 formed by the clamping members 308 and 310 to allow for the medical assistant to pull the first and second sides of the finger cuff 104 through the opened clamping slot 322 while attached to a patient's finger and thereafter the clamping members 308 and 310 hold the first and second sides of the finger cuff 104 firmly together when pressure is no longer applied by the medical assistant to the opposed descending sides 302 and 304 such that finger cuff 104 is firmly attached to the patient's finger.

As can be seen in diagram 510, the clamp mechanism, as set forth in the previous description, may be utilized to apply the finger cuff 104 to a finger, such as a large sized finger. Similarly, with reference to diagram 520, the clamp mechanism, as set forth in the previous description, may likewise be utilized to apply the finger cuff 104 to a medium sized finger. Moreover, with reference to diagram 530, the clamp mechanism, as set forth in the previous description, may likewise be utilized to apply the finger cuff 104 to a small sized finger. In this way, a finger cuff 104 may be utilized for any finger size of the patient such that the clamp mechanism provides a one-size-fits-all solution.

Figure 6A:
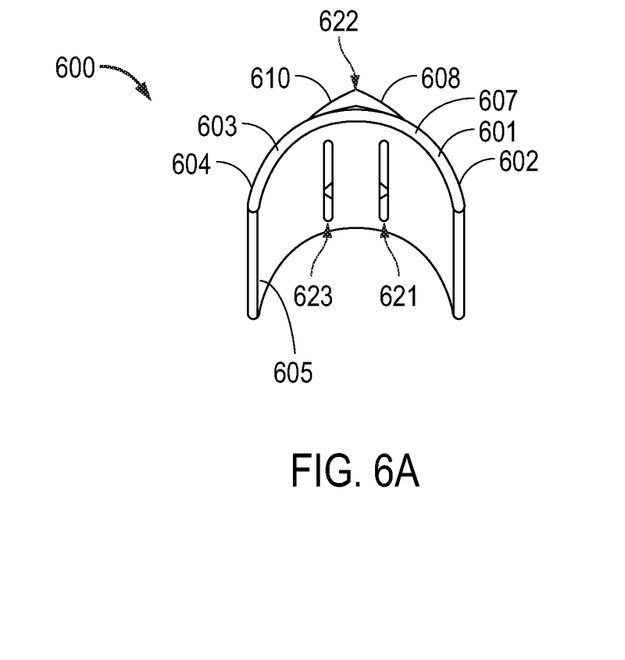
FIGS. 6A-6B are views of another embodiment of a clamp mechanism.
Figure 6B:
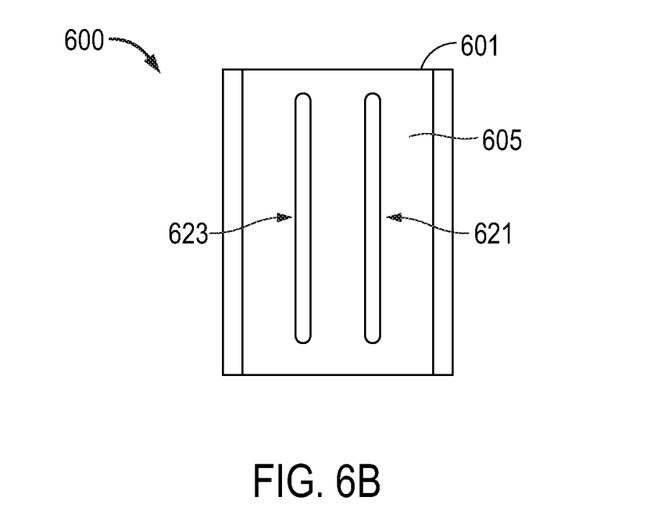

With additional reference to FIGS. 6A-6B, another embodiment of a clamp mechanism 600, will be described. It should be appreciated that clamp mechanism 600 is substantially similar to the previously described clamp mechanism 300. In similar fashion to the clamp mechanism 300, clamp mechanism 600 includes a mounting structure 601 and a pair of opposed clamping members 608 and 610. In particular, mounting structure 601 includes a top portion 607, opposed descending side 602 and 604, and an exterior surface and an interior surface 603 and 605. Further, the top portion 607 includes a gap portion, but, in this embodiment, the gap portion includes a first gap 621 and a second gap 623, that are separate and adjacent to one another, and, as will be described, separately accept the first and second sides 105 and 106 of the finger cuff 104, respectively.

Additionally, similar to clamp mechanism 300, the pair of opposed clamping members 608 and 610 extend from opposites sides of the exterior 603 of the mounting structure 601 to form a clamping slot 622 over the first and second gaps 621 and 623. Clamping slot 622 may be openable by the medical assistant applying pressure to the opposed descending sides 602 and 604 to open the clamping slot 622 to allow for the pulling of the first and the second sides 105 and 106 of the finger cuff 104 by the medical assistant through the first and second adjacent gaps 621 and 623 and through the open clamping slot 622, in tandem, by the medical assistant. Moreover, the clamping slot 622 is closable by the medical assistant releasing pressure to the opposed descending sides 602 and 604 such that the first and second sides 105 and 106 of the finger cuff 104 are clamped together by the opposed clamping members 608 and 610 such that the finger cuff 104 may be firmly attached to the patient's finger, as has been previously described in detail.

Thus, in this embodiment, similar to previously described embodiment of the clamp mechanism 300, the opposed descending sides 602 and 604 of the clamp mechanism 600 are suitably flexible to allow for the opening of the clamping slot 622 formed by the clamping members 608 and 610 when pressure is applied by the medical assistant to the opposed descending sides 602 and 604 to allow for the pulling of the first and second sides 105 and 106 of the finger cuff 104 through the open clamping slot 622 and through each of the first gap and the second gaps 621 and 623 of the mounting structure 601, respectively, in tandem. Further, the opposed descending sides 602 and 604 are suitably flexible to allow the clamping members 608 and 610 to clamp together to close the clamping slot 622 to hold the first and second sides 105 and 106 of the finger cuff 104 firmly together when pressure is no longer applied by the medical assistant to the opposed descending sides 602 and 604 such that the finger cuff 104 may be firmly attached to the patient's finger, as has been previously described in detail.

Therefore, embodiments of the invention relate to a clamp mechanism that may be utilized by a medical assistant to assist in attaching a finger cuff to a patient's finger. By utilizing the previously described techniques, attaching a finger cuff to a patient's finger is made much easier than currently utilized techniques. Further, because the attachment time period to attach the finger cuff is shortened, the time period to obtain blood pressure measurements is significantly quicker than previous utilized techniques. Moreover, by utilizing the previously described embodiments of the invention, a one-size-fits-all finger cuff may be used instead of common place small, medium, and large sized finger cuffs.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A clamp mechanism to assist in attaching a finger cuff having a first side and a second side to a patient's finger by a medical assistant, the clamp mechanism comprising:
   a mounting structure including a top portion, opposed descending sides, and an exterior and an interior, the top portion including a gap; and
   a pair of opposed clamping members that extend from opposite sides of the exterior of the mounting structure to form a single clamping slot over the gap, wherein the clamping slot is openable to allow for the pulling of the first side and the second side of the finger cuff by the medical assistant through the gap and the opened clamping slot, and wherein the clamping slot is closeable such that the first side and the second side of the finger cuff are clamped together at the clamping slot by the opposed clamping members so that the finger cuff is firmly attachable to the patient's finger.

2. The clamp mechanism of claim 1, wherein the mounting structure is approximately arch-shaped.

3. The clamp mechanism of claim 2, wherein the opposed clamping members each extend from the exterior of the arch-shaped mounting structure to form an approximate triangle shape over the gap and to provide the clamping slot over the gap.

4. The clamp mechanism of claim 1, wherein the opposed descending sides are suitably flexible to allow for the opening of the clamping slot formed by the clamping members when pressure is applied by the medical assistant to the opposed descending sides to allow for the pulling of the first and second sides of the finger cuff through the opened clamping slot.

5. The clam mechanism of claim 4, wherein the opposed descending sides are suitably flexible to allow the clamping members to clamp together to close the clamping slot to hold the first and second sides of the finger cuff firmly together when pressure is no longer applied by the medical assistant to the opposed descending sides.

6. The clamp mechanism of claim 1, wherein the gap of the top portion of the mounting structure comprises a first gap and a second gap, in which the first gap and the second gap are separate and adjacent to one another.

7. The clamp mechanism of claim 6, wherein the opposed descending sides are suitably flexible to allow for the opening of the clamping slot formed by the clamping members when pressure is applied by the medical assistant to the opposed descending sides to allow for the pulling of the first and second sides of the finger cuff through the opened clamping slot and to allow for the pulling of the first and second sides of the finger cuff through each of the first gap and the second gap of the top portion of the mounting structure, respectively, in tandem.

8. The clam mechanism of claim 7, wherein the opposed descending sides are suitably flexible to allow the clamping members to clamp together to close the clamping slot to hold the first and second sides of the finger cuff firmly together when pressure is no longer applied by the medical assistant to the opposed descending sides.

9. The clamp mechanism of claim 1, wherein each of the opposed clamping members includes a saw-tooth structure to form the clamping slot to clamp the first side and the second side of the finger cuff together.

10. A method to assist attaching a finger cuff having a first side and a second side to a patient's finger by a medical assistant by utilizing a clamping mechanism that includes: a mounting structure having a gap and pair of opposed descending sides, and a pair of opposed clamping members that extend from the pair of opposed descending side to form a single clamping slot over the gap; the method comprising:
   opening the clamping slot formed by the clamping members by the medical assistant applying pressure to the opposed descending sides to allow for the pulling of the first side and the second side of the finger cuff by the medical assistant through the gap and the opened clamping slot; and
   closing the clamping slot by the medical assistant no longer applying pressure to the opposed descending sides to hold the first and second sides of the finger cuff firmly together at the clamping slot by the opposed clamping members so that the finger cuff is firmly attachable to the patient's finger.

11. The method of claim 10, wherein the mounting structure is approximately arch-shaped.

12. The method of claim 11, wherein the opposed clamping members each extend from the exterior of the arch-shaped mounting structure to form an approximate triangle shape over the gap and to provide the clamping slot over the gap.

13. The method of claim 10, wherein the opposed descending sides are suitably flexible to allow for the opening of the clamping slot formed by the clamping members when pressure is applied by the medical assistant to the opposed descending sides to allow for the pulling of the first and second sides of the finger cuff through the opened clamping slot.

14. The method of claim 13, wherein the opposed descending sides are suitably flexible to allow the clamping members to clamp together to close the clamping slot to hold the first and second sides of the finger cuff firmly together when pressure is no longer applied by the medical assistant to the opposed descending sides.

15. The method of claim 10, wherein the gap of the mounting structure comprises a first gap and a second gap, in which the first gap and the second gap are separate and adjacent to one another.

16. The method of claim 15, wherein the opposed descending sides are suitably flexible to allow for the opening of the clamping slot formed by the clamping members when pressure is applied by the medical assistant to the opposed descending sides to allow for the pulling of the first and second sides of the finger cuff through the opened clamping slot and to allow for the pulling of the first and second sides of the finger cuff through each of the first gap and the second gap of the mounting structure, respectively, in tandem.

17. The method of claim 16, wherein the opposed descending sides are suitably flexible to allow the clamping members to clamp together to close the clamping slot to hold the first and second sides of the finger cuff firmly together when pressure is no longer applied by the medical assistant to the opposed descending sides.

18. The method of claim 10, wherein each of the opposed clamping members includes a saw-tooth structure to form the clamping slot to clamp the first side and the second side of the finger cuff together.

19. A blood pressure measurement system to measure a patient's blood pressure comprising:
a finger cuff having a first side and a second side attachable to a patient's finger by a medical assistant, the finger cuff to measure the patient's blood pressure; and
a clamp mechanism to assist the medical assistant in attaching the finger cuff to the patient, the clamp mechanism comprising:
a mounting structure including a top portion, opposed descending sides, and an exterior and an interior, the top portion including a gap; and
a pair of opposed clamping members that extend from opposite sides of the exterior of the mounting structure to form a single clamping slot over the gap, wherein the clamping slot is openable to allow for the pulling of the first side and the second side of the finger cuff by the medical assistant through the gap and the opened clamping slot, and wherein the clamping slot is closeable such that the first side and the second side of the finger cuff are clamped together at the clamping slot by the opposed clamping members so that the finger cuff is firmly attachable to the patient's finger.

20. The blood pressure measurement system of claim 19, wherein the mounting structure is approximately arch-shaped.

21. The blood pressure measurement system of claim 20, wherein the opposed clamping members each extend from the exterior of the arch-shaped mounting structure to form an approximate triangle shape over the gap and to provide the clamping slot over the gap.

22. The blood pressure measurement system of claim 19, wherein the opposed descending sides are suitably flexible to allow for the opening of the clamping slot formed by the clamping members when pressure is applied by the medical assistant to the opposed descending sides to allow for the pulling of the first and second sides of the finger cuff through the opened clamping slot.

23. The blood pressure measurement system of claim 22, wherein the opposed descending sides are suitably flexible to allow the clamping members to clamp together to close the clamping slot to hold the first and second sides of the finger cuff firmly together when pressure is no longer applied by the medical assistant to the opposed descending sides.

24. The blood pressure measurement system of claim 19, wherein the gap of the top portion of the mounting structure comprises a first gap and a second gap, in which the first gap and the second gap are separate and adjacent to one another.

25. The blood pressure measurement system of claim 24, wherein the opposed descending sides are suitably flexible to allow for the opening of the clamping slot formed by the clamping members when pressure is applied by the medical assistant to the opposed descending sides to allow for the pulling of the first and second sides of the finger cuff through the opened clamping slot and to allow for the pulling of the first and second sides of the finger cuff through each of the first gap and the second gap of the top portion of the mounting structure, respectively, in tandem.

26. The blood pressure measurement system of claim 25, wherein the opposed descending sides are suitably flexible to allow the clamping members to clamp together to close the clamping slot to hold the first and second sides of the finger cuff firmly together when pressure is no longer applied by the medical assistant to the opposed descending sides.

27. The blood pressure measurement system of claim 19, wherein each of the opposed clamping members includes a saw-tooth structure to form the clamping slot to clamp the first side and the second side of the finger cuff together.

* * * * *